(12) United States Patent
Lee et al.

(10) Patent No.: US 11,114,207 B2
(45) Date of Patent: Sep. 7, 2021

(54) MEDICAL SYSTEM CAPABLE OF ARTIFICIAL INTELLIGENCE AND INTERNET OF THINGS

(71) Applicant: National Cheng Kung University, Tainan (TW)

(72) Inventors: Shuenn-Yuh Lee, Tainan (TW); Yu-Jin Lin, Changhua County (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 324 days.

(21) Appl. No.: 16/195,379

(22) Filed: Nov. 19, 2018

(65) Prior Publication Data
US 2019/0156949 A1 May 23, 2019

(30) Foreign Application Priority Data

Nov. 20, 2017 (TW) .................................. 106140179
Oct. 11, 2018 (TW) .................................. 107135861

(51) Int. Cl.
*G16H 50/20* (2018.01)
*G16H 40/60* (2018.01)
(Continued)

(52) U.S. Cl.
CPC ........... *G16H 50/20* (2018.01); *A61B 5/0022* (2013.01); *A61B 5/024* (2013.01); *A61B 5/369* (2021.01); *A61B 5/389* (2021.01); *A61B 5/4041* (2013.01); *A61N 1/36031* (2017.08); *A61N 1/36139* (2013.01); *A61N 1/3782* (2013.01); *A61N 1/37223* (2013.01); *G06N 20/00* (2019.01); *G16H 40/60* (2018.01); *H04L 67/125* (2013.01);
(Continued)

(58) Field of Classification Search
CPC ...... G16H 50/20; G06N 20/00; A61B 5/0022; A61B 5/0024; A61B 5/0476; A61B 5/0488; A61B 5/4041; A61B 5/4836; A61B 5/7275; A61N 1/36031; A61N 1/36139; A61N 2/002
See application file for complete search history.

(56) References Cited

FOREIGN PATENT DOCUMENTS

TW       201612843 A       4/2016

OTHER PUBLICATIONS

Official action issued by Taiwan Intellectual Property Office dated Oct. 24, 2019.

*Primary Examiner* — Thaddeus B Cox
(74) *Attorney, Agent, or Firm* — Chun-Ming Shih; Lanway IPR Services

(57) ABSTRACT

A medical system capable of artificial intelligence and Internet of Things includes a conditioner, a control terminal device and a computation device. A patient may perform a physiological tissue stimulation treatment through the conditioner, which may adjust a stimulation parameter according to a feedback result of the stimulation, and transmits a signal of a feedback result indicative of an abnormal stimulation through the Internet of Things to the control terminal device, which has a disease analysis module built therein capable of further identifying an abnormal signal indicative of a disease and the physiological tissue for the feedback result indicative of the abnormal stimulation, so that a medical caring staff adjusts the stimulation parameter for the conditioner with respect to the abnormal signal. Moreover, the medical caring staff may interact with the computation device through the control terminal device to perform a big data analysis for optimization of the stimulation treatment.

14 Claims, 11 Drawing Sheets

(51) Int. Cl.
*A61N 1/36* (2006.01)
*A61N 1/372* (2006.01)
*A61N 1/02* (2006.01)
*H04L 29/08* (2006.01)
*G06N 20/00* (2019.01)
*A61B 5/024* (2006.01)
*A61B 5/00* (2006.01)
*A61N 1/378* (2006.01)
*A61B 5/369* (2021.01)
*A61B 5/389* (2021.01)
*A61N 2/00* (2006.01)
*A61N 5/06* (2006.01)

(52) U.S. Cl.
CPC .............. *A61N 1/025* (2013.01); *A61N 2/002* (2013.01); *A61N 5/06* (2013.01); *A61N 2005/0626* (2013.01)

MEDICAL SYSTEM CAPABLE OF ARTIFICIAL INTELLIGENCE AND INTERNET OF THINGS

CROSS-REFERENCE TO RELATED APPLICATIONS

This application claims the priority of Republic of China Patent Application Nos. 106140179 and 107135861 filed on Nov. 20, 2017 and Oct. 11, 2018, respectively, in the State Intellectual Property Office of the R.O.C., the disclosure of which is incorporated herein by reference.

BACKGROUND OF THE INVENTION

Field of the Invention

The invention relates to a neural stimulation treatment technology, in particular to a medical system capable of artificial intelligence and Internet of Things.

Descriptions of the Related Art

Existing stimulators in the market are mainly divided into two types with respect to stimulations, including in vitro and in vivo stimulations, and are subdivided into various types of devices due to different stimulation positions. In general, an in vitro stimulator is mostly used for rehabilitation treatment, which is mainly an open loop system, and stimulates a specific portion based on magnitudes of configured stimulation amplitude, frequency, and time length, while an in vivo stimulator belongs to its dedicated corresponding stimulator based on different organs, such as a heart, brain epilepsy, brain Parkinson stimulator, in the form of an open loop, for a specific stimulation treatment.

The in vivo and in vitro stimulators mentioned above are dedicated stimulators designed based on stimulation positions, and cannot be adapted for adequate use depending on different positions. Moreover, most the in vitro stimulators are bulky, such that they are not only difficult to carry, but also lack of closed loop feedback in use, so that the feedback condition after stimulation cannot be detected. Users can only adjust the relevant stimulation parameters based on their own feelings, so that not only the use is complex, but also there is a considerable degree of uncertainty. Usually, only experience can be relied on to configure magnitudes of configured stimulation amplitude, frequency level, and time length, such that double effort results in half effect. Furthermore, the in vivo stimulators differ due to different stimulated organs as well, so that universal functions cannot be achieved because each portion requires a dedicated stimulator. Moreover, a complete closed loop feedback system is lacking, so that adequate stimulation parameters cannot be adapted automatically based on effect of stimulation treatment. Mostly, determination of stimulation parameters relies on a doctor. In addition, unfriendly user interfaces result in considerable degree of difficulty in use.

From the above, those skilled in the art strive for seeking out one system capable of AI (Artificial Intelligence) and easy change of stimulation parameters for implementation of customized stimulation parameter settings to achieve optimized stimulation effect.

SUMMARY OF THE INVENTION

In view of the shortcomings of the prior art mentioned above, the present invention provides a medical system capable of artificial intelligence and Internet of Things, which has an artificial intelligence machine learning function, can adapt individualized stimulation parameters automatically.

Another object of the present invention is to provide a medical system capable of artificial intelligence and Internet of Things, and the medical system capable of artificial intelligence and Internet of Things provides a friendly user interface allowing a medical caring staff to adjust the stimulation parameters.

Further object of the present invention is to provide a medical system capable of artificial intelligence and Internet of Things, and the medical system capable of artificial intelligence and Internet of Things provides a widely applicable stimulator capable of providing several different stimulation approaches, including electrical stimulation, magnetic stimulation, optical stimulation and the like, which can provide corresponding stimulation approach, magnitudes of amplitude, frequency level, and time length based on different stimulation positions.

According to the above purpose and another purpose of the invention, the invention is to provide a medical system capable of artificial intelligence and Internet of Things including: a conditioner, a control terminal device and a computation device, a conditioner including: a stimulation unit used to perform stimulation processing on a physiological tissue to be stimulated; a detection unit for detecting a physiological signal of a physiological tissue to be detected; a digital controller for performing digital signal processing on the physiological signal detected by the detection unit and analyzing a state of the stimulation processing performed on the physiological tissue to be stimulated to obtain a feedback result after the stimulation processing, the digital controller including: a storage unit storing conditioning parameter data for conditioning at least one physiological tissue, the control parameter data including: a first stimulation parameter value, a second stimulation parameter value and a predictable response signal; an open loop unit causing the stimulation unit to stimulate the physiological tissue to be stimulated according to the first stimulation parameter value stored in the storage unit; a closed loop unit capable of feeding back the predictable response signal by determining that the physiological tissue to be detected, which is detected by the detection unit, stimulates the physiological tissue to be stimulated with the first stimulation parameter value in the stimulation unit, followed by a stimulation parameter setup with the first stimulation parameter value, and causing the stimulation unit to stimulate the physiological tissue to be stimulated with the first stimulation parameter value; on the contrary, the closed loop unit determining that the stimulation unit performs stimulation with the first stimulation parameter value, while the physiological tissue to be detected, which is detected by the detection unit, does not feedback the predictable response signal, such that the stimulation unit stimulates the physiological tissue to be stimulated with the second stimulation parameter value instead, and it is determined whether the physiological tissue to be detected, which is detected by the detection unit, can feedback the predictable response signal when the physiological tissue to be stimulated performs stimulation with the second stimulation parameter value, for a feedback result with an abnormal message to be output if the expected response signal is not fed back; and a conditioning end wireless transmission unit for wireless transmission of the feedback result processed by the digital controller, or wireless reception of the conditioning parameter data to be processed by the digital controller; and a computation device including: a cloud database for storing response values from stimulation performed on a plurality of physiological tissues with a plurality of stimulation parameter values; a server module for accessing the cloud database, the server module providing a cloud user interface for inputting desired settings or storing at least one updated stimulation parameter value of the at least one physiological tissue, or updating the predictable response signal of the at least one physiological tissue, or for displaying the feedback result of the at least one physiological tissue to be inquired and the stimulation parameter value used by the feedback result; and a control terminal device including: a near-end transmission unit for performing data transmission processing with the conditioning end wireless transmission unit to perform an access action on the storage unit; a far-end transmission unit for performing data transmission with the server module; an intelligent processing module for processing data received by the near-end transmission unit and the far-end transmission unit, and controlling the near-end transmission unit and the far-end transmission unit to transmit data, as well as providing an end user interface, which displays the feedback result of the physiological tissue to be detected that is due to the physiological tissue to be stimulated being stimulated, received by the near-end transmission unit, or sets up the updated stimulation parameter value with which the conditioner performs the stimulation processing, wherein the updated stimulation parameter value is transmitted to the digital controller through the near-end transmission unit and the conditioning end wireless transmission unit for processing, wherein the digital controller that outputs the abnormal message uses the received updated stimulation parameter value for the stimulation unit to stimulate the physiological tissue to be stimulated, and the closed loop unit determines whether the physiological tissue to be detected can feedback the predictable response signal when the physiological tissue to be stimulated performs stimulation with the updated stimulation parameter value, such that the feedback result of the abnormal message is output if the expected response signal is not fed back, wherein can let the intelligent processing module provide subsequent update processing on the conditioning parameter data according to the abnormal message.

Preferably, in the medical capable of artificial intelligence and Internet of Things, wherein the computation device further includes: a learning module, wherein the server module receives the conditioning parameter data, with which the physiological tissue to be stimulated is stimulated, transmitted from the intelligent processing module, and the physiological tissue to be detected does not feedback the predictable response signal, then the cloud database creates a stimulation parameter update record, based on which a medical staff analyzes and transmits an updated stimulation parameter value to the storage unit of the conditioner through the intelligent processing module, for the closed loop unit to cause the stimulation unit to stimulate the physiological tissue to be stimulated with the updated stimulation parameter value, as well as the aforementioned detection for the feedback result of the physiological tissue to be detected is repeated, and a stimulation target signal is found out until the physiological tissue to be stimulated is stimulated and the physiological tissue to be detected can feedback a predictable stimulation feedback signal, for the learning module to store the stimulation parameter target value in the cloud database.

Compared to the conventional technology, the medical system capable of artificial intelligence and Internet of Things proposed by the present invention can provide a variety of stimuli, including electrical, optical, and magnetic stimuli, and can be further applicable to various portions of a body for treatment of multiple diseases. Also, the conditioner mentioned above is capable of Internet of Things, and can allow a medical staff to use via a user interface of a control terminal device (such as a smartphone, a personal digital assistant or a computer) instantly for adjusting magnitudes of amplitude, frequency level and time length of stimulus. Moreover, the control terminal device or the computation device mentioned above further utilizes artificial intelligence and learning algorithm, can perform disease identification and analysis based on feedback result of stimulation processing, as well as gives corresponding stimulation treatment simultaneously, and feeds back the stimulation effect to achieve the optimized stimulation treatment.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
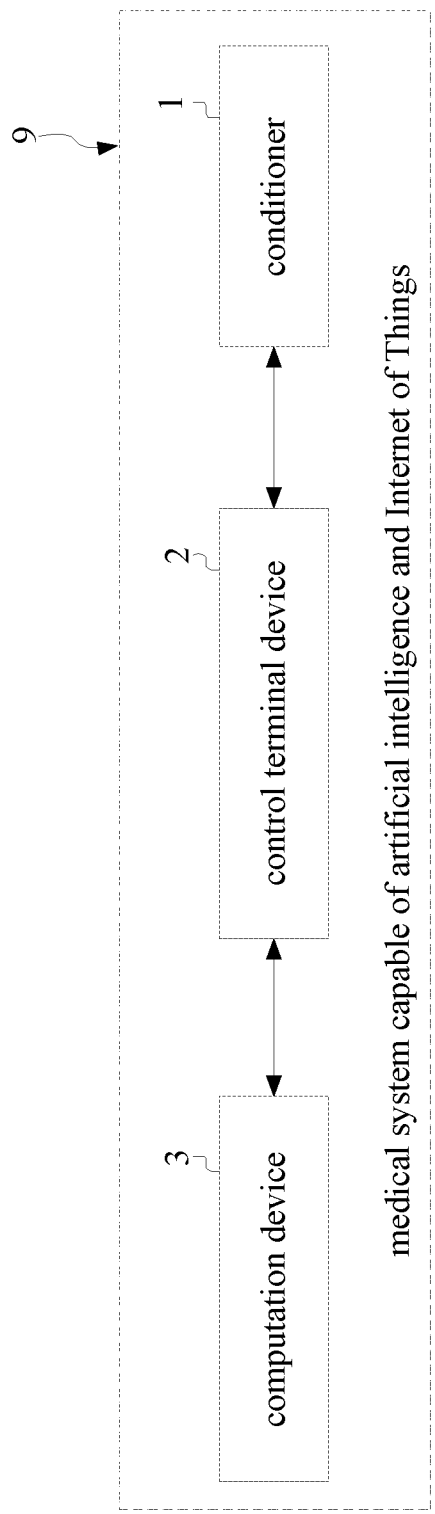
FIG. 1 is a schematic view showing a system architecture of an example of the medical system capable of artificial intelligence and Internet of Things according to the present invention.

Embodiments of the present invention will now be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art. In the drawings, the shapes and dimensions of elements may be exaggerated for clarity, and the same reference numerals will be used throughout to designate the same or like components.

Refer to FIG. 1, which is a schematic view showing a system architecture of a medical system capable of artificial intelligence and Internet of Things according to the present invention. As shown in FIG. 1, a medical system capable of artificial intelligence and Internet of Things 9 includes at least a conditioner 1, at least a control terminal device 2 and at least a computation device 3. The conditioner 1 mentioned above is, for example, an in vivo or in vitro stimulator for detecting and stimulating physiological signals such as heart rhythm, brain wave, electromyographic signal or neural signal etc., and a person under detection, such as a patient, may have the conditioner 1 implanted (i.e., the in vivo stimulator mentioned above) therein or worn (i.e., the in vitro stimulator mentioned above) thereon as needed. The control terminal device 2 mentioned above is, for example, a smartphone, a digital assistant device or an electronic device such as a computer. A medical caring staff or a person under detection may configure stimulation parameters for the conditioner 1 via the control terminal device 2, or receive and process or display a stimulation feedback result of a physiological tissue of the person under detection detected and stimulated from the conditioner 1 by the control terminal device 2. The computation device 3, such as a cloud equipment, is used for storing various response values of a plurality of physiological tissues stimulated with a plurality of stimulation parameter values, and may collect stimulation feedback results from detection and stimulation performed on the person under detection by the conditioner 1 as well as the stimulation parameters transmitted by the control terminal device 2, for a big data analysis to be performed by collecting stimulation parameters of the physiological tissues and the stimulation feedback results, such that the computation device 3 performs an artificial intelligence algorithm, and performs a disease identification and analysis to correct the stimulation parameters of the physiological tissues, followed by transmitting the corrected stimulation parameters to the conditioner 1 via the control terminal device 2 mentioned above for the conditioner 1 to provide the person under detection with a corresponding stimulation treatment, and feedback a stimulation effect in order for optimization of the stimulation treatment.

Figure 4:
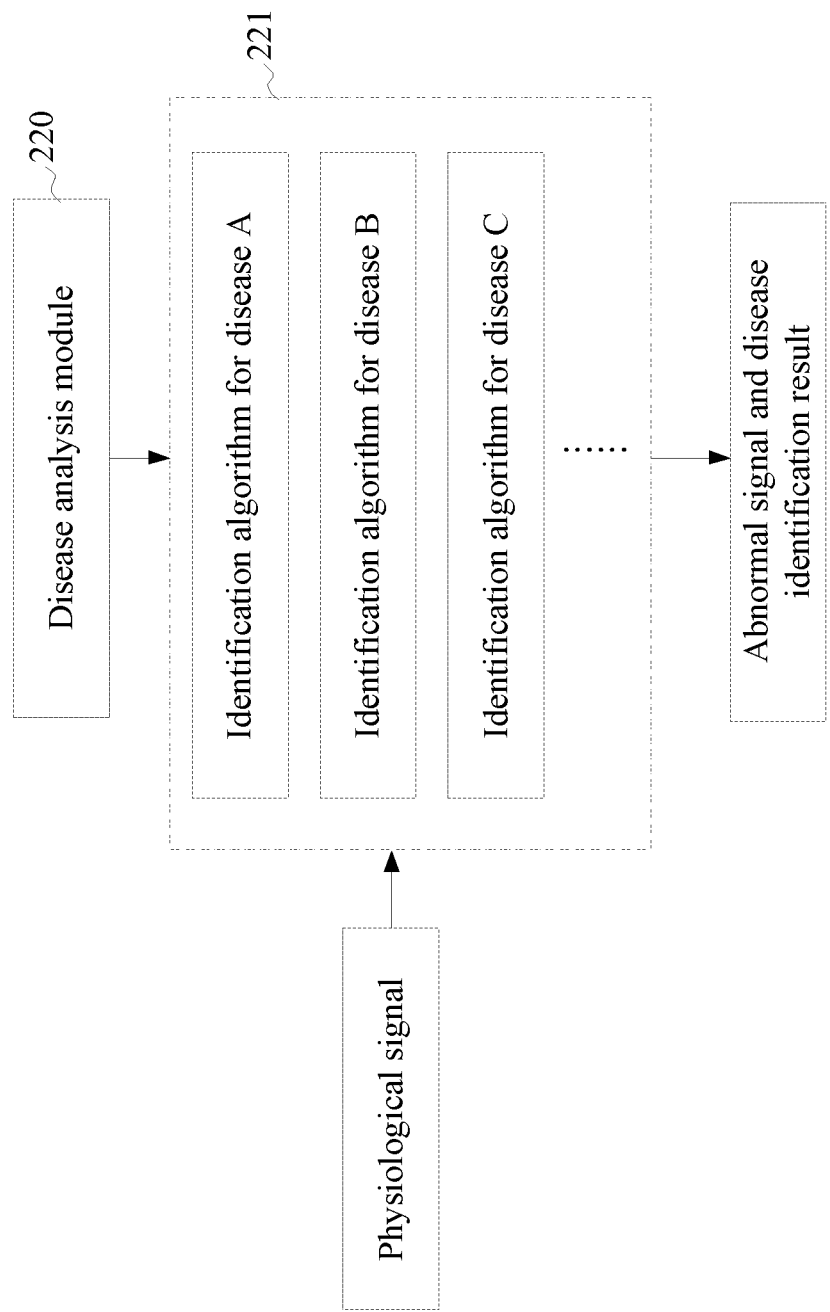
FIG. 4 is a flow chart showing processing steps of a control terminal device performing disease analysis processing of the medical system capable of artificial intelligence and Internet of Things according to the present invention.

In particular, the artificial intelligence algorithm (as shown in FIG. 4 below) performed by the computation device 3 mentioned above performs identification and analysis of a disease to correct the stimulation parameters of the physiological tissues. The artificial intelligence algorithm may also be performed on the control terminal device 2 mentioned above to assist a medical caring staff in quick analysis and determination of the disease.

Figure 2:
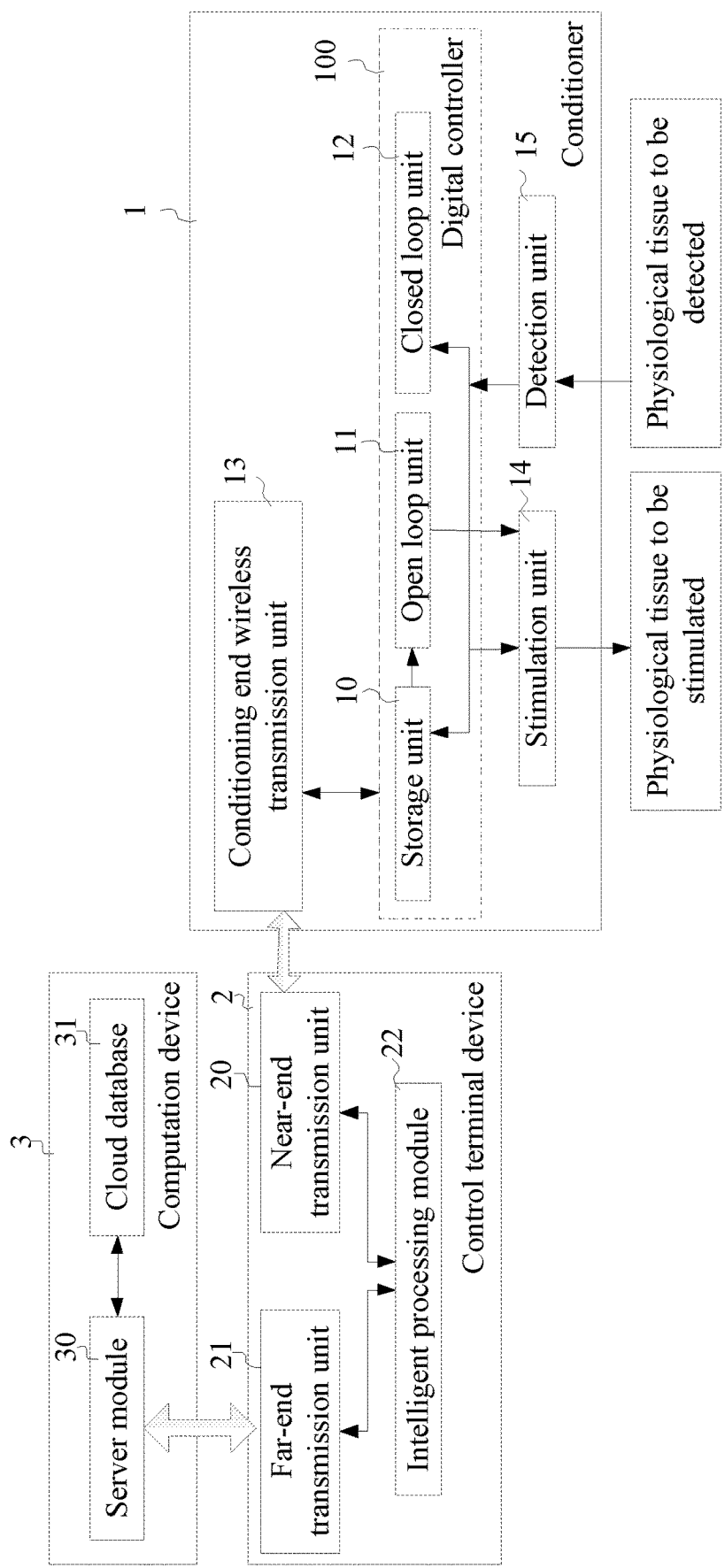
FIG. 2 is a basic architectural diagram showing various system members of the medical system capable of artificial intelligence and Internet of Things according to the present invention.

Refer to FIG. 2, which shows a basic architectural diagram of various system members of a medical system capable of artificial intelligence and Internet of Things according to the present invention. For simplicity of description, this example is only for functional elements related to main features of each system member of a medical system capable of artificial intelligence and Internet of Things according to the present invention, while other functions, such as input components, microprocessors, power supplies, and the like, together with the functions thereof will be omitted. The conditioner 1 in this example includes a storage unit 10, an open loop unit 11, a closed loop unit 12, a conditioning end wireless transmission unit 13, a stimulation unit 14 and a detection unit 15. The stimulation unit 14 is used to perform stimulation processing on a physiological tissue to be stimulated. The detection unit 15 is used for detecting a physiological signal of a physiological tissue to be detected. It should be noted that the physiological to be stimulated tissue mentioned above and the physiological tissue to be detected mentioned above may be the same tissue position or different tissue positions, depending on the requirements for the desired physiological tissue to be treated with stimulation. The following examples are described by way of different body positions. The storage unit 10 is used for storing conditioning parameter data for conditioning at least a physiological tissue, the control parameter data including: a first stimulation parameter value, a second stimulation parameter value and a predictable response signal. The open loop unit 11 causes the stimulation unit 14 to stimulate the physiological tissue to be stimulated according to the first stimulation parameter value stored in the storage unit 10. The closed loop unit 12 determines that the physiological tissue to be detected, which is detected by the detection unit 15, performs stimulation with the first stimulation parameter value at the stimulation unit to be capable of feeding back a predictable response signal, and then the stimulation parameter is configured with the first stimulation parameter value for the stimulation unit 14 to stimulate the physiological tissue to be stimulated with the first stimulation parameter value; on the contrary, the closed circuit unit 12 determines that the physiological tissue to be detected, which is detected by the detection unit, stimulates the physiological tissue to be stimulated with the first stimulation parameter value at the stimulation unit without feeding back the predictable response signal, so that the stimulation unit 14 stimulates the physiological tissue to be stimulated with the second stimulation parameter value instead, and determines whether the predictable response signal can be fed back when the physiological tissue to be detected stimulates the physiological tissue to be stimulated with the second stimulation parameter value at the stimulation unit; wherein, the determined feedback result may be stored in the storage unit 10. The conditioning end wireless transmission unit 13 transmits the feedback result stored in the storage unit 10, or receives the conditioning parameter data to be written into the storage unit 10. The conditioning end wireless transmission unit 13 may be implemented by a wireless radio frequency circuit (illustrated in FIG. 6 below).

The control terminal device 2 in this example includes a near-end transmission unit 20, a far-end transmission unit 21 and an intelligent processing module 22. It should be noted that, in order to simplify the drawing and description, the control terminal device 2 shown in FIG. 2 shows only members related to the present invention, other unrelated members, such as input units such as control keys, or microprocessors, etc. are not shown in the drawings of the present invention. The near-end transmission unit 20 is used for performing data transmission processing with the conditioning end wireless transmission unit 13 of the conditioner 1 to perform processing, such as accessing or updating conditioning parameters, for the storage unit 10. Moreover, the near-end transmission unit 20 and the conditioning end wireless transmission unit 13 use the Internet of Things wireless network for data transmission processing. The far-end transmission unit 21 is used to perform data transmission with the computation device 3. The intelligent processing module 22 is used to process the data received by the near-end transmission unit 20 and the far-end transmission unit 21, and control the near-end transmission unit 20 and the far-end transmission unit 21 to perform transmission of data. The intelligent processing module 22 is, for example, an application software, which provides a digital signal processing function to process effectively the physiological signals transmitted by the conditioner 1, and may provide an end user interface for displaying the feedback result of the physiological tissue due to stimulated physiological tissue to be stimulated, which is received by the near-end transmission unit 20, via the end user interface, or for a near-end user (such as a patient under physiological signal detection, a family member or a medical caring staff thereof etc.) to configure an updated stimulation parameter value, which is used to condition the conditioner 1 for performing stimulation processing, via the end user interface, wherein the updated stimulation parameter value is transmitted to the storage unit 10 for storage through the near-end transmission unit 20 and the conditioning end wireless transmission unit 13.

Figure 3:
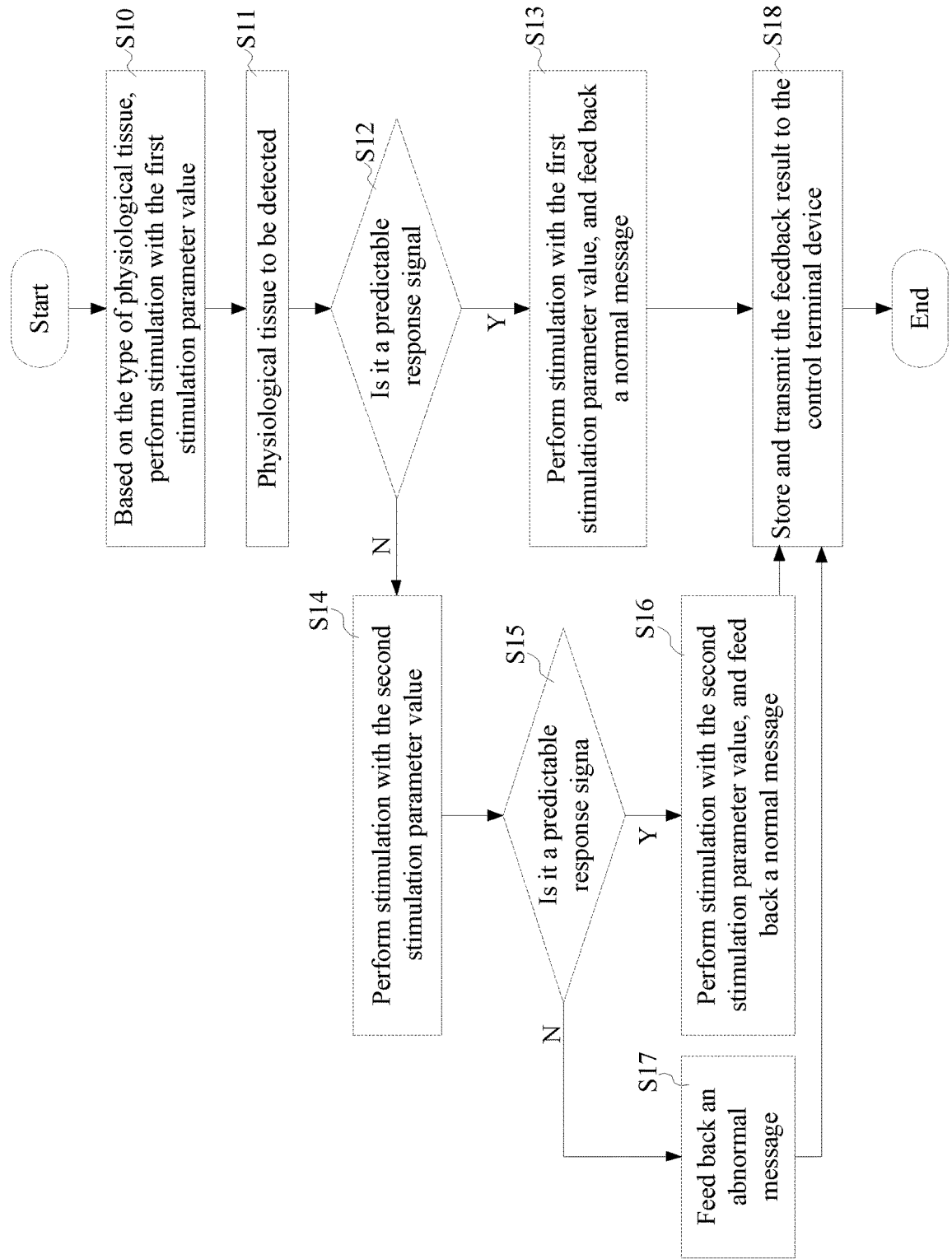
FIG. 3 is a flow chart showing processing steps of a conditioner performing a stimulation algorithm of the medical system capable of artificial intelligence and Internet of Things according to the present invention.

In the virtual box as shown in FIG. 2, unit members of the storage unit 10, the open loop unit 11 and the closed loop unit 12 enclosed in the virtual box may integrate functions thereof for a digital controller 100 to implement the stimulation processing mentioned above and the determination of feedback result, as well as be capable of amplifying and filtering the collected physiological signal, and encoding the physiological signal detected by the detection unit 15 through an encryption encoding algorithm circuit, followed by transmission to the control terminal device 2 through the conditioning end wireless transmission unit 13. Moreover, the storage unit 10, the open circuit unit 11 and the closed loop unit 12 have programmable designs, and can receive user instructions transmitted from the control terminal device 2 through the conditioning end wireless transmission unit 13 (for example, through the stimulation parameters configured via the end user interface mentioned above). Together with corresponding operations, the neural conditioning for feedback control may be performed through a built-in stimulation algorithm (as shown in FIG. 3). Furthermore, the open loop unit 11 and the closed loop unit 12 provide an artificial intelligence preprocessing (AI preprocessing) stimulation algorithm, which can initially perform characterization and feature classification on the physiological signals detected by the detection unit 15 to accelerate the AI disease identification algorithm (as shown in FIG. 4).

For the stimulation algorithm as shown in FIG. 3, a digital controller consisting of the storage unit 10, the open loop unit 11 and the closed loop unit 12 performs step S10 at first. The storage unit 10 has stored corresponding stimulation parameters according to the positions to be detected and stimulated. That is, there are different stimulation parameters for different physiological tissues. Here, a physiological tissue is stimulated with a first stimulation parameter value by the stimulation unit 14.

Next, step S11 is performed, in which the detection unit 15 detects the physiological signal fed back by the physiological tissue. It is to be noted additionally that the physiological tissue to be stimulated, on which the stimulation unit 14 performs the stimulation processing, and the physiological tissue to be detected, on which the detection unit 15 performs detection processing, may be the same tissue body position or different tissue body positions, depending on the requirements for the physiological tissue to be stimulated for treatment.

Next, step S12 is performed. According to the predictable response signal stored in the storage unit 10, the physiological signal fed back by the physiological tissue and detected by the detection unit 15 is checked with respect to matching or mismatching. In case of matching, step S13 is performed. On the contrary, if the fed back physiological signal does not match the predictable response signal stored in the storage unit 10, step S14 is performed.

In step S13, the stimulation unit 14 continues to stimulate the physiological tissue with the first stimulation parameter value, and feedback a normal message, followed by performing step S18.

In step S14, the stimulation unit 14 stimulates the physiological tissue with the second stimulation parameter value instead, followed by performing step S15.

In step S15, according to the predictable response signal stored in the storage unit 10, the physiological signal fed back by the physiological tissue and detected by the detection unit 15 is checked with respect to matching or mismatching. In case of matching, step S16 is performed. On the contrary, if the fed back physiological signal does not match the predictable response signal stored in the storage unit 10, step S17 is performed.

In step S16, the stimulation unit 14 continues to stimulate the physiological tissue with the second stimulation parameter value, and feedback a normal message, followed by performing step S18.

In step S17, an abnormal message is fed back, followed by performing step S18.

In step S18, the physiological signal detected by the detection unit 15 and the feedback result are stored in the storage unit 10, and the feedback result is transmitted to the control terminal device 2 through the conditioning end wireless transmission unit 13 for analysis or further processing.

The near-end transmission unit 20 of the control terminal device 2 receives the feedback result sent in the step S18 mentioned above. The processing performed by the intelligent processing module 22 may involve: storing the feedback result, and notifying a far-end user (for example, a family member or a medical caring staff for a patient under detection of a physiological signal) by using a communication method such as a short message or a communication software, or notifying a near-end user (for example, a patient under detection of physiological signal, a family member thereof or a medical caring staff) by an output device such as a speaker or a display at the local end of the control terminal device 2. The medical caring staff may further adjust the stimulation parameter values via the end user interface provided by the intelligent processing module 22, followed by transmission to the conditioner 1 through the near-end transmission unit 20 to achieve the purpose of adjusting the stimulation parameters.

In addition to providing the end user interface and the digital signal processing function for processing the physiological signal transmitted by the conditioner 1, the intelligent processing module 22 further has a disease analysis module 220, which utilizes an artificial intelligence technology to analyze a disease in real time. As shown in FIG. 4, the disease analysis module 220 provides multiple disease identification algorithms 221 for analyzing a physiological signal transmitted by the conditioner 1 to identify whether the physiological signal fed back by the conditioner 1 is an abnormal signal instantly, and identify the disease type of which the abnormal signal is indicative. The real-time artificial intelligence disease analysis assists a doctor in diagnosis.

Refer to FIG. 2 again, the computation device 3 includes a cloud database 31 and a server module 30. The cloud database 31 is used for storing response values from stimulation performed on a plurality of physiological tissues with a plurality of stimulation parameter values, and storing multiple disease identification algorithms and stimulation parameter values for performing stimulation treatment on various diseases. The server module 30 is used to access the cloud database 31, the server module 30, and the far-end transmission unit 21 of the control terminal device 2 for data transmission, and store the data transmitted by the far-end transmission unit 21 of the control terminal device 2 in the cloud database 31. The control terminal device 2 may update or add the disease identification algorithms at a local end of the control terminal device 2, and the stimulation parameter values with which stimulation treatment is performed on multiple diseases. Relatively, the control terminal devices 2 in various places may also upload the received physiological signals as well as the abnormal signals and disease identification results after analysis to the computation device 3, which may perform a big data analysis thereby to find a more accurate disease stimulation treatment method. Accordingly, the demand for remote medical care may be satisfied.

Furthermore, the server module 30 further provides a cloud user interface for inputting desired settings or storing an updated stimulation parameter value of at least a physiological tissue, or updating a predictable response signal of a physiological tissue, or for displaying the feedback result of a physiological tissue to be inquired and the stimulation parameter value used by the feedback result.

The aforementioned computation device 3 further has a learning module (not shown here). After a medical caring staff performs adjustment for stimulation parameter values via the end user interface provided by the intelligent processing module 22 of the control terminal device 2, followed by transmission to the conditioner 1 through the near-end transmission unit 20, the closed loop unit 12 stimulates the physiological tissue to be stimulated with the adjusted stimulation parameter values (i.e., the updated stimulation parameter values mentioned above), as well as the stimulation algorithm as shown in FIG. 3 is repeated to determine the feedback result of the physiological tissue to be detected, and find out a stimulation target signal until the physiological tissue to be stimulated is stimulated and the physiological tissue to be detected can feedback a predictable stimulation feedback signal. Finally, the learning module of the computation device 3 stores the stimulation parameter target value in the cloud database 31 for subsequent access by other medical caring staffs.

Figure 5:
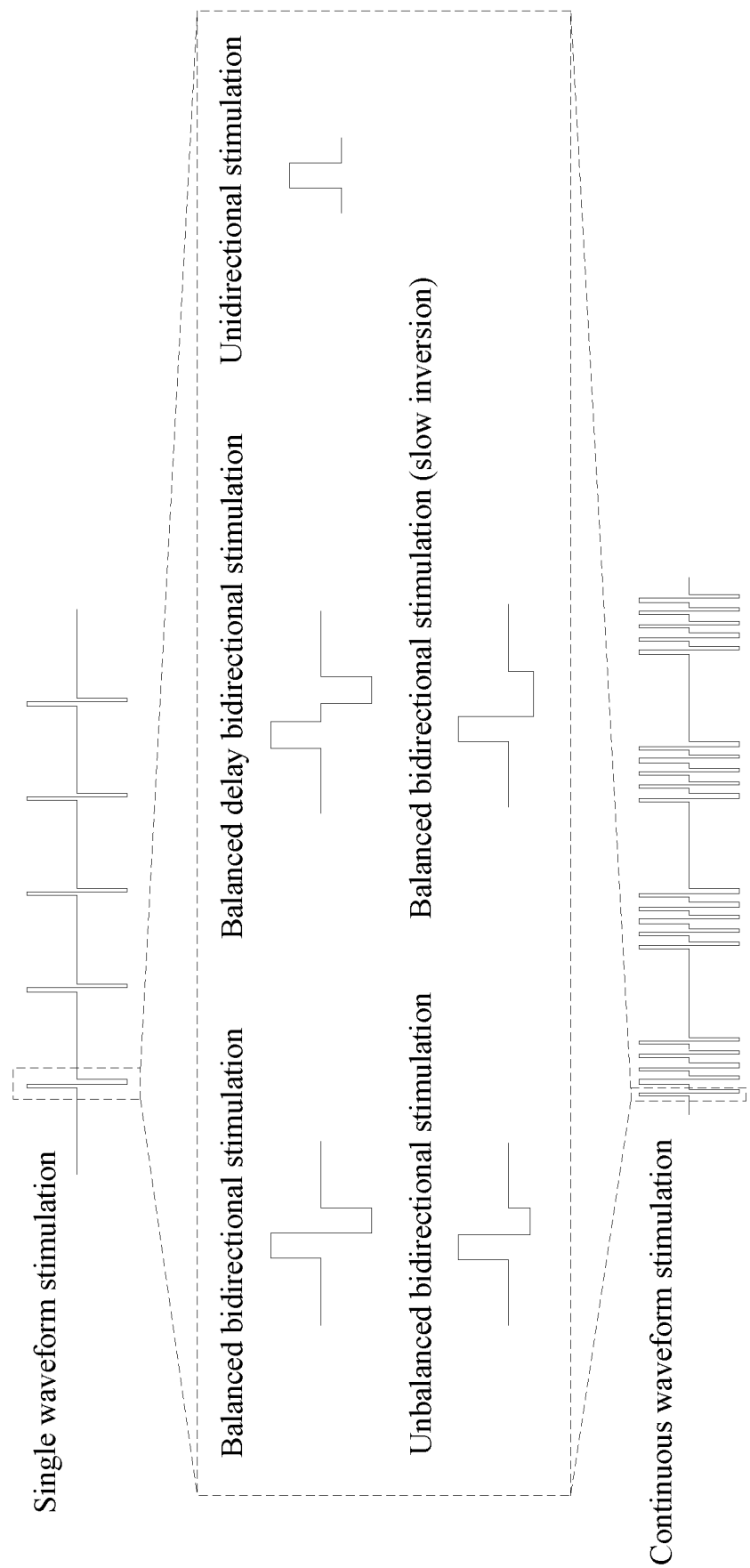
FIG. 5 shows different stimulation waveforms that can be provided by a stimulation unit of the medical system capable of artificial intelligence and Internet of Things according to the present invention.

The conditioner 1 in the medical system capable of artificial intelligence and Internet of Things 9 according to the present invention has a stimulation algorithm "capable of adjusting individualized stimulation parameters according to individual stimulation feedbacks automatically", which utilizes "open, closed loop systems to adjust individualized stimulation parameters according to individual stimulation feedbacks automatically", as well as the digital controller 100 has pre-stored stimulation parameter values of various physiological tissues, and may integrate the stimulation unit 14 having various different stimulation approaches (including electrical stimulation, magnetic stimulation, optical stimulation, etc.), to provide corresponding stimulation approaches (including balanced bidirectional stimulation, balanced delay bidirectional stimulation, unbalanced bidirectional stimulation, unidirectional stimulation, balanced bidirectional stimulation and the like, which are as shown in FIG. 5), magnitude of amplitude, frequency level and time length for different stimulation positions, so that the conditioner 1 may become a widely applicable stimulator.

In the medical system capable of artificial intelligence and Internet of Things 9 according to the present invention mentioned above, in order for the conditioner 1 to transmit the detected physiological signal to the control terminal device 2 at any time, the power consumption for the conditioning end wireless transmission unit 13 of the conditioner 1 needs to be emphasized. Please refer to FIG. 6, which shows a system block diagram showing a basic architecture for the conditioning end wireless transmission unit 13 of the conditioner 1. In order for the conditioner 1 to be applicable to Internet of Things, a harmonic detection technology is utilized, thereby simplifying the system circuit design, to achieve the purpose of reducing power consumption and area, and facilitating integration. The conditioning end wireless transmission unit 13 includes a wireless radio frequency transmission module 130 and a wireless radio frequency receiving module 135.

The wireless radio frequency transmission module 130 includes a pre-emphasis signal generator 131, a current-reused self-mixing voltage-controlled oscillator 132, and a current-reused multiple-transconductance power amplifier 133. Generally, the pre-emphasis signal generator 131 is used to perform shaping of signal waveform on digital signals from the Internet of Things (IOT), and modulate and output the digital signals as modulated output signals. The current-reused self-mixing voltage-controlled oscillator 132 utilizes a self-mixing technique to increase voltage/current amplitude of the modulated output signals and reduce phase noise. The current-reused multiple-transconductance power amplifier 133 utilizes a current reuse technique to amplify the voltage/current amplitude of the modulated output signals, and sends the modulated output signals after being amplified to a wireless channel through a first antenna 134a.

In particular, the wireless radio frequency transmission module 130 has characteristics of low power consumption, low area, low cost, high degree of integration and easy accomplishment, etc., making it applicable to an IOT system. The wireless radio frequency transmission module 130 can modulate any input signal (such as digital signal or analog signal) in a manner of frequency up or down conversion. As shown in Figure, when digital signals from the IOT enter the wireless radio frequency transmission module 130, they first undergo signal waveform shaping performed by the pre-emphasis signal generator 131 to form modulated output signals. The signal waveform shaping can be done in various ways to compensate possible shortcomings of different modulation methods such as OOK modulation, ASK modulation, FSK modulation, PSK modulation, QPSK modulation, QAM modulation, MSK modulation and so on. This not only solves a problem of slow amplitude change of OOK signals and ASK signals, but also speeds up stability of frequency modulation of FSK signals as well as solves a high-frequency interference problem of discontinuous PSK signals and QPSK signals.

After being processed by the pre-emphasis signal generator 131, the digital signals have become the modulated output signals that are sent to the current-reused self-mixing voltage-controlled oscillator 132. The current-reused self-mixing voltage-controlled oscillator 132 utilizes the self-mixing technique while operates with lower power consumption, lower component area and lower cost to raise voltage/current amplitude of the modulated output signals and have lower phase noise and lower noise skin, thereby making the wireless radio frequency transmission module 130 less interference with other frequency bands.

Then, the modulated output signals from the current-reused self-mixing voltage-controlled oscillator 132 are sent to the current-reused multiple-transconductance power amplifier 133. The current-reused multiple-transconductance power amplifier 133 utilizes the current reuse technique, an amplifier cascode architecture and a DC block, etc. to form a power amplifier that can produce an arbitrary multiple of transconductance, so as to output higher output power to the first antenna 134a under lower power consumption, such that the use of the current-reused multiple-transconductance power amplifier 133 may achieve higher energy conversion benefits. Moreover, the amplifier cascode architecture can simply use a single bias current to accomplish even harmonic elimination function and common mode noise elimination function that usually are only possessed by a differential architecture. This improves linearity of the modulated output signals, reduces interference with neighbor channels, improves signal-to-noise ratio (SNR) of the wireless radio frequency receiving module 135, and reduces bit-error rate of the wireless radio frequency receiving module 135.

The wireless radio frequency receiving module 135 includes a balun self-biasing gain-bandwidth-improved envelope detector 136 and a current-reused cascode-two-stage amplifier 138. Generally, the balun self-biasing gain-bandwidth-improved envelope detector 136 is used to detect carrier input signals received from a second antenna 134b to obtain baseband signals, and modulate the baseband signals to form differential signals. The current-reused cascode-two-stage amplifier 138 is used to perform several times of amplification in an open loop state to amplify voltage/current amplitude of the modulated differential signals to form output signals, and send the output signals to a digital controller 100.

Preferably, the wireless radio frequency receiving module 135 further includes a tunable high-pass filter 137, which can be mounted between the balun self-biasing gain-bandwidth-improved envelope detector 136 and the current-reused cascode-two-stage amplifier 138. The tunable high-pass filter 137 is used to filter off intermediate/low frequency noise from the differential signals.

Preferably, the wireless radio frequency receiving module 135 further includes a comparator 139 connected to and situated next to the current-reused cascode-two-stage amplifier 138. The comparator 139 is used to detect the output signals that have been amplified by the current-reused cascode-two-stage amplifier 138, convert the output signals into digital data, and send the digital controller 100 performs stimulation on a physiological tissue and performs a stimulation algorithm as illustrated in FIG. 3 mentioned above.

Figure 6:
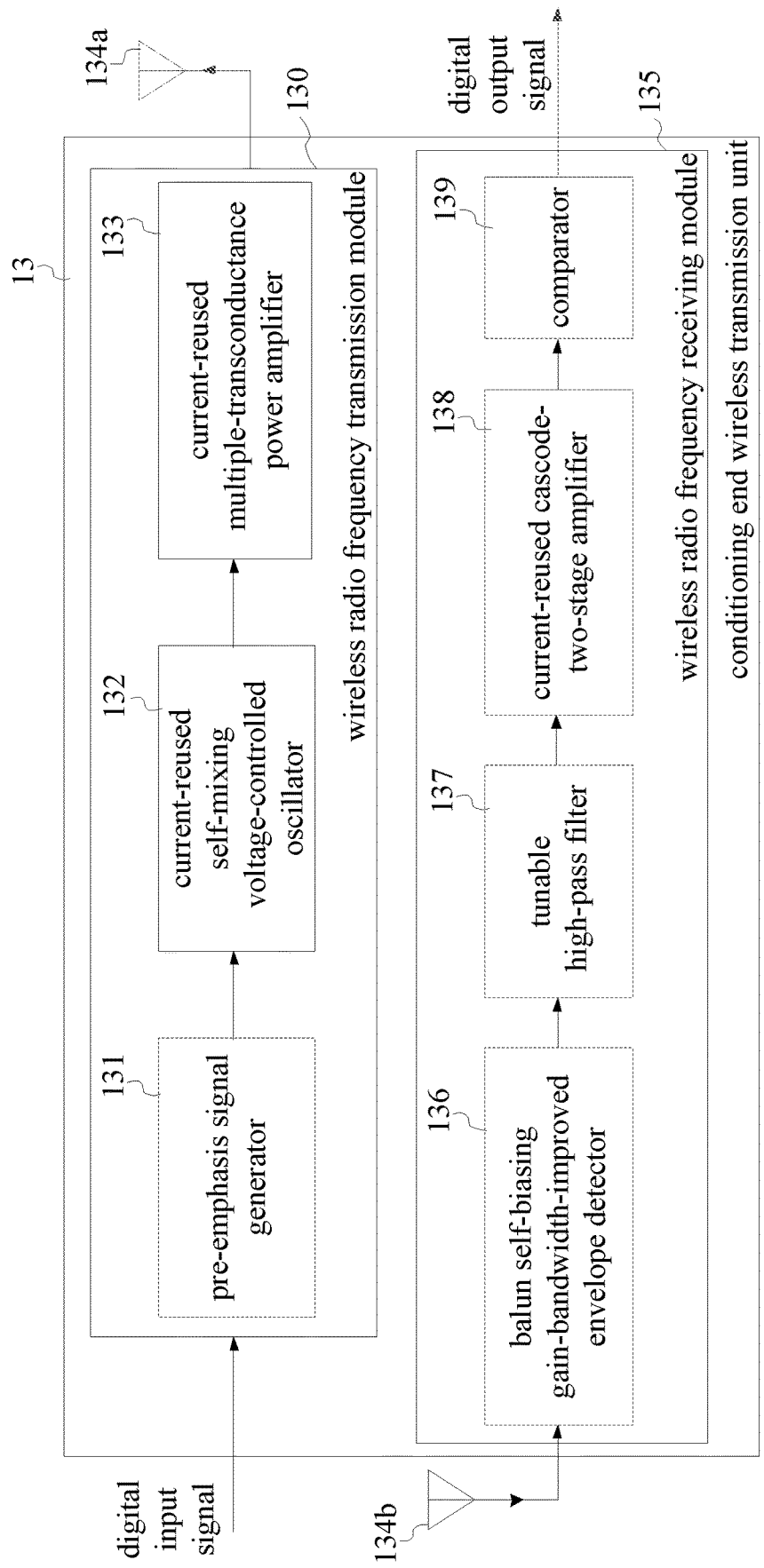
FIG. 6 is a system block diagram showing a basic architecture for a conditioning end wireless transmission unit of a conditioner.

Particularly, the wireless radio frequency receiving module 135 has characteristics of low power consumption, low area, low cost, high degree of integration and easy accomplishment, etc., making it applicable to the IOT system. The wireless radio frequency receiving module 135 utilizing the harmonic detection technique does not need a phase-locked loop (PLL) in the transmission part of the wireless radio frequency transceiver system 1, thereby greatly reducing power consumption, area and cost of the wireless radio frequency transmission module 130, as well as improving integration of the conditioning end wireless transmission unit 13. The wireless radio frequency receiving module 135 can demodulate any amplitude-modulated signal, such as ASK signal, OOK signal, PSK signal or QPSK signal. As shown in FIG. 6, the second antenna 134b receives the carrier input signals and sends them to the balun self-biasing gain-bandwidth-improved envelope detector 136 where baseband envelopes of the signals are detected and turned into differential signals for being outputted. As demodulated signals if changing directly to baseband are subjected to low frequency flicker noise interference, the differential signals after demodulation are sent to the tunable high-pass filter 137. The tunable high-pass filter 137 can have a tunable frequency band design in order to resist process offset.

Afterwards, the differential signals are sent to the current-reused cascode-two-stage amplifier 138 where several times of amplification are performed. This is because the demodulated signals do not have large amplitude, so an amplifier is needed. For the current-reused cascode-two-stage amplifier 138, in the open loop state, a cascode amplifier has advantages of lower power consumption and better bandwidth, and a two-stage amplifier has advantages of better gain and larger output swing. Finally, the amplified differential signals are sent to the comparator 139. If the differential signals are digital signals, the comparator 139 converts them into digital data that can be outputted to the digital controller 100.

The wireless radio frequency transmission module 130 utilizes a direct up-conversion technique to modulate baseband signals, thereby having characteristics of low system complexity and low power consumption, and output signals therefrom can be modulated by OOK (on-off-keying) or FSK (frequency-shift-keying) method. If using OOK modulation, the wireless radio frequency transmission module 130 may have characteristics of low power consumption, low area, low cost, low complexity and high degree of integration. If using FSK modulation, the wireless radio frequency transmission module 130 may have characteristics of high data rate and low bit error rate.

The wireless radio frequency transmission module 130 utilizes the harmonic detection technique and thus can resist carrier frequency offset, such that PLL is not required in the wireless radio frequency transmission module 130. Further in the wireless radio frequency transceiver system, the wireless radio frequency transmission module 130 always has higher power consumption than the wireless radio frequency receiving module 135. No PLL needed can thus significantly reduce power consumption and area of the wireless radio frequency transmission module 130.

When the conventional wireless radio frequency transceiver system utilizes the direct up-conversion technique to process transmission, bias voltage/current of a voltage-controlled oscillator must be controlled in an amplitude-shift keying (ASK) procedure to control the voltage-controlled oscillator to output large/small amplitude so as to generate amplitude modulated signals. However, time for the outputted signal amplitude from the voltage-controlled oscillator to go up and down may limit or affect signal bit rate during transmission. This means that, if the time for the amplitude to go up and down is long after the voltage-controlled oscillator is subjected to the voltage/current control, the system bit rate is reduced; if the time for the amplitude to go up and down is short after the voltage-controlled oscillator is subjected to the voltage/current control, the system bit rate is raised. To solve the above problem, the wireless radio frequency transmission module 130 the current-reused self-mixing voltage-controlled oscillator 132 is provided at its front end with the pre-emphasis signal generator 131, so as to weight signal amplitude of voltage/current control signals that are originally to be inputted to the current-reused self-mixing voltage-controlled oscillator 132, and through the total weighting, generate stimulation signals with arbitrary waveform. The stimulation signals are inputted to the current-reused self-mixing voltage-controlled oscillator 132 to make up and down change of its amplitude subjected to stronger signal control to accelerate the up and down change, such that signal bit rate of the entire wireless radio frequency transmission module 130 can be greatly increased. In another embodiment, if the pre-emphasis signal generator 131 is implemented in the form of digital circuit, it merely consumes very low power, and thus the signal bit rate of the entire wireless radio frequency transmission module 130 would be raised with the power consumption being hardly increased.

As described above, the pre-emphasis signal generator 131 allows the signal bit rate of the entire wireless radio frequency transmission module 130 to be increased. For example, if using the OOK modulation method, the wireless radio frequency transmission module 130 has lower bit rate than using the ASK modulation method. It is because when sending OOK signal 0 (a modulation index of OOK modulation is 100%), the current-reused self-mixing voltage-controlled oscillator 132 is in a fully off state; while using the ASK modulation method, the current-reused self-mixing voltage-controlled oscillator 132 is not fully closed (off). When transmitting OOK modulated signals, every time to send out signal 1, it has to wait until the current-reused self-mixing voltage-controlled oscillator 132 restarts oscillating from the fully off state and then signal 1 can be sent out. That is, to completely transmit signal 0 and signal 1, every time it has to wait until the current-reused self-mixing voltage-controlled oscillator 132 restarts oscillating from the fully off state. This waiting time makes bit rate of the OOK modulated signals not able to increase. The pre-emphasis signal generator 131 may shorten the time required for the current-reused self-mixing voltage-controlled oscillator 132 to restart oscillating, and thus improves the bit rate of the OOK modulated signals, thereby making the OOK modulation method advantageously have low power consumption and effectively solve the problem of having low bit rate.

If the wireless radio frequency transmission module 130 of the invention uses the FSK (frequency-shift-keying) modulation method, the pre-emphasis signal generator 131 can change input signals and output tunable bias voltage/current of the current-reused self-mixing voltage-controlled oscillator 132, wherein through different ratio weighted control waveform, the current-reused self-mixing voltage-controlled oscillator 132 is stable and fast in a frequency modulation process so as to raise signal bit rate when transmitting FSK modulated signals.

The current-reused self-mixing voltage-controlled oscillator 132 utilizes a current-reused self-mixing technique to transmit radio frequency oscillator signals to a frequency doubler where double-frequency radio frequency signals are produced. Then, the double-frequency signals are subjected to frequency transfer by a cross coupling mixer of the current-reused self-mixing voltage-controlled oscillator 132 to become radio frequency signals with original frequency, which are then sent to an LC tank of the current-reused self-mixing voltage-controlled oscillator 132. This forms a positive feedback loop, which may enhance amplitude of output signals from the LC tank of the current-reused self-mixing voltage-controlled oscillator 132 and equivalently reduce phase noise of the output signals. In the above operation, the LC tank, the cross coupling mixer and the frequency doubler all use the current reuse technique to reduce consumption of required current and use the self-mixing technique to reduce phase noise of the output signals, such that larger oscillation signals can be outputted without increasing a bias current path.

The current-reused multiple-transconductance power amplifier 133 of the invention adopts a combination of DC block and transconductor to form such a multiple-transconductance amplifier. As power consumption of a power amplifier in a transmission process is relatively considerable, in the current-reused multiple-transconductance power amplifier 133 of the invention, the DC block serves as the ground for AC signals, and the transconductor can share a single DC path in a cascode manner to have bias, and further the DC block performs AC coupling so as to superimpose output AC signals, such that the multiple-transconductance effect is achieved and overall transconductance can be any multiple. This is significantly better than a conventional current reuse technique by which equivalent output transconductance (Gm) of a power amplifier is 2 times of Gm of a transistor.

During a current reuse process, if voltage swing of output signals is not large, there is no need to worry about transistor swing, thereby allowing an arbitrary multiple of transconductance to be achieved by any transistor cascode. In the current-reused multiple-transconductance power amplifier 133 of the invention, as input signals are differential signals and usually even harmonic components are in the same direction in a two-end output architecture, reverse differential signals in the invention can be superimposed in the same direction at an output end while even harmonic of the signals in the same direction would have reverse elimination. This thus accomplishes even harmonic elimination in an architecture using merely one bias current, which otherwise can only be achieved in a conventional differential power amplifier.

Figure 7:
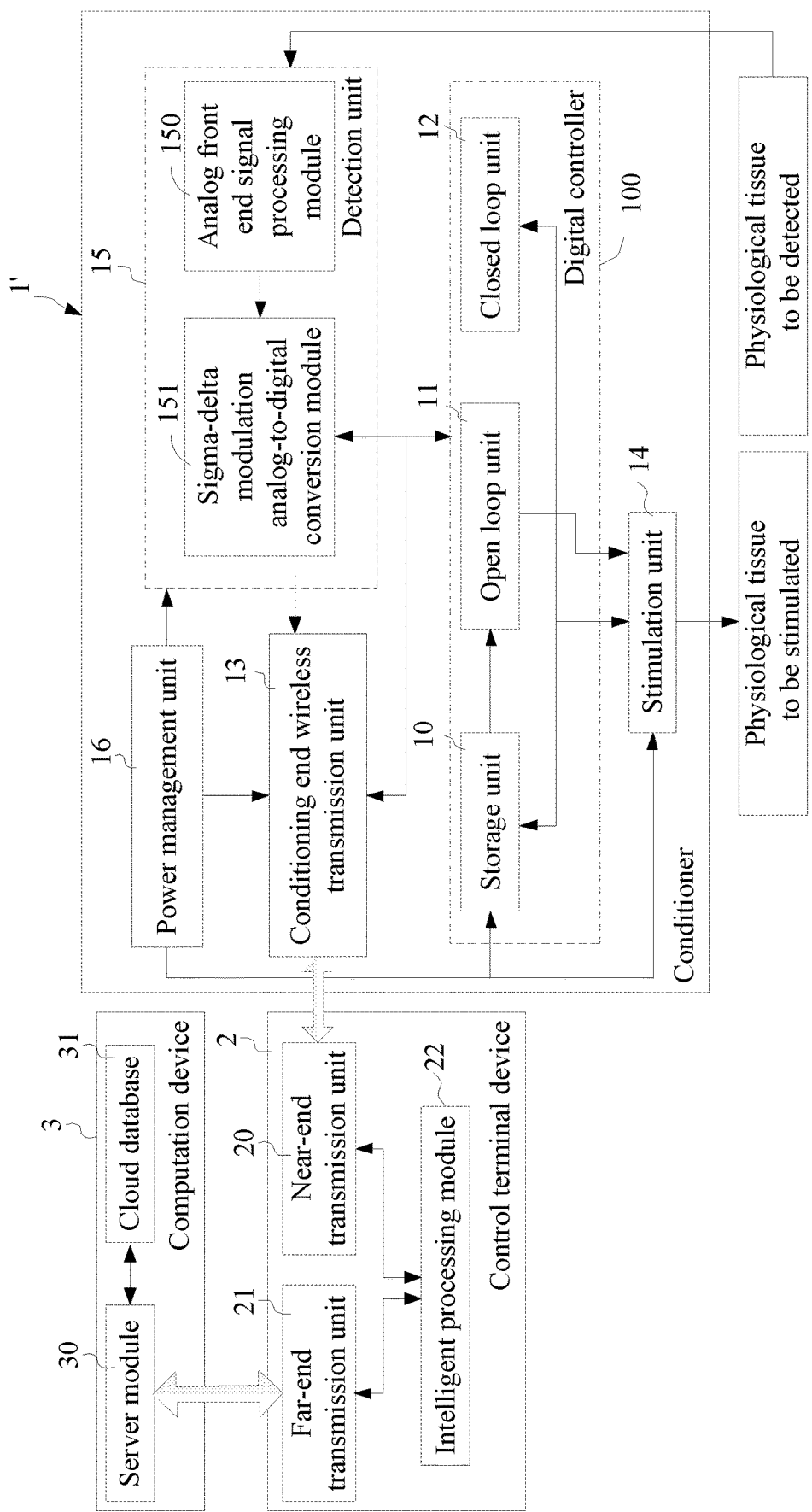
FIG. 7 is a schematic view showing a system architecture of another example of the medical system capable of artificial intelligence and Internet of Things according to the present invention.
Figure 8:
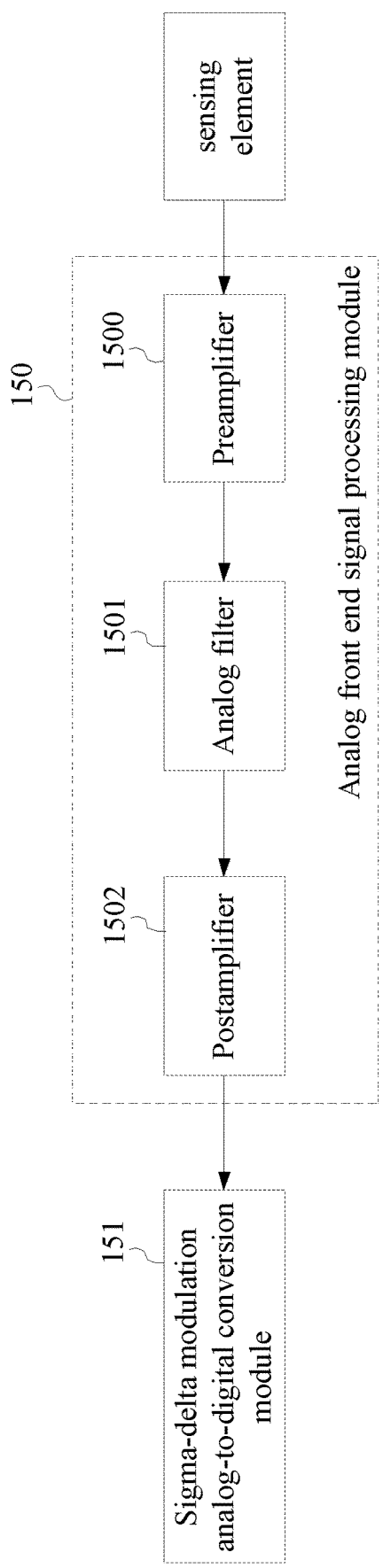
FIG. 8 is a system block diagram showing built-up members of a detection unit shown in FIG. 7.

Since the evolution of integrated circuit design requires not only high efficiency, but also low cost and low power consumption, the detection unit 15, which detects physiological signals, for the conditioner of the medical system according to the present invention includes an analog front end signal processing module 150 and a sigma-delta modulation analog-to-digital conversion module 151, as shown in FIG. 7. The analog front end signal processing module 150 includes a preamplifier 1500, an analog filter 1501, and a postamplifier 1502 as shown in FIG. 8. The analog front end signal processing module 150 starts operation once obtaining a DC stabilized voltage from a power management unit 16. The physiological signal sensed by a sensing element from the detection unit 15 may be a weak signal, so that the physiological signal is subject to a first signal amplification via the preamplifier 1500 to generate an amplified sensed physiological signal for analysis processing performed on the physiological signal by subsequent circuits. The physiological signals for different physiological tissues have different signal frequency bands over the frequency spectrum. Therefore, the analog filter 1501 is used for filtering the amplified sensed physiological signals to filter out unwanted noise and extract filtered signals over the frequency band occupied by the physiological signal. The filtered signal is further subject to a second amplification performed by the postamplifier 1502 to generate a dynamic range required to meet the subsequent sigma-delta modulation analog-to-digital conversion module 151, and is converted into a digital physiological signal by the sigma-delta modulation analog-to-digital conversion module 151 for the digital controller 100 to perform digitalization processing.

The design of the analog filter 1501 may include log pass filter, high pass filter, band pass filter, band rejection filter or the combination thereof, such as series combination, but not limited hereto. The design of the preamplifier 1500 or the postamplifier 1502 may include open loop amplifier or closed loop amplifier, but not limited hereto. The design of the analog filter 1501 may be continuous time process circuit or discrete time process circuit, but not limited hereto.

Next, refer to FIG. 7 again, the sigma-delta modulation analog-to-digital conversion module 151 in the conditioner 1' is characterized by automatic correction of dynamic range and low power consumption, monitors the strength of the physiological signal transmitted by the analog front end signal processing module 150 dynamically, change in strength of physiological signal, may reduce or increase system order, or change feedforward coefficients to save system power consumption. The sigma-delta modulation analog-to-digital conversion module 151 compares the physiological signal to be output to the digital controller 100 for processing with the physiological signal transmitted by the analog front end signal processing module 150 and calculates multiple sets of dynamic range curves by a dynamic extension algorithm, based on which the digital controller 100 extracts a suitable combination of system orders and feedforward coefficients for storage. The digital controller 100 inputs a preset signal and gives a set of system orders and feedforward coefficients for system circuit adjustment and initialization. The strength of the signal output by the sigma-delta modulation analog-to-digital conversion module 151 is monitored dynamically. When the digital controller 100 monitors that the change in the strength of the output physiological signal does not exceed a preset value, initial feedforward coefficients and system orders are maintained. Otherwise, the feedforward coefficients and the system orders are switched until the system is stable and the power/performance balance is reached. In a wide dynamic extension algorithm, the requirement for high resolution output is achieved by adjusting the architecture and the feedforward coefficients, and the introduced application scenario of an adjustable system architecture involves that: when the strength of the signal output from the system is large enough, there is no need to use a high-order sigma-delta modulation technology for analog-to-digital conversion, that is, the use of a low-order architecture may reduce power consumption of the system effectively; on the contrary, when the strength of the output signal is weaker, the order is increased to improve system performance. Therefore, the sigma-delta modulation analog-to-digital conversion module 151 focuses on the overall performance, especially on having good signal resolution and low power consumption design technology.

Figure 9:
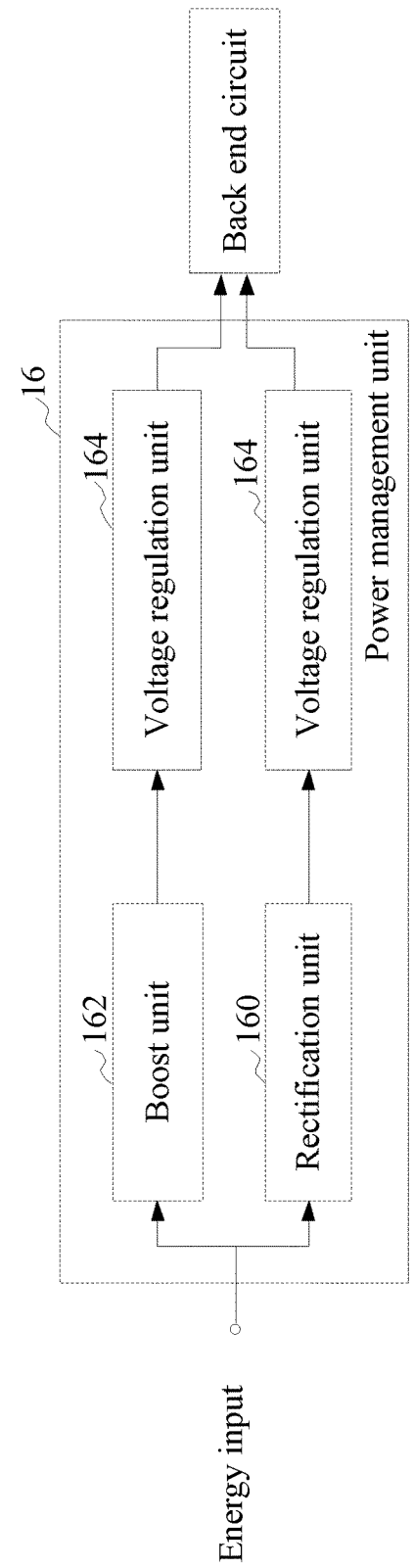
FIG. 9 is a system block diagram showing built-up members of a power management unit shown in FIG. 7.

The power consumption due to the detection processing of physiological signal is reduced by the detection unit 15 mentioned above and the conditioning end wireless transmission unit 13 utilizes a harmonic detection technology to achieve demodulation, so that the complexity of the wireless radio frequency receiving module may be simplified significantly to reduce power consumption of the system. Moreover, power supply with low power and reduction of energy loss of elements are also considered, as shown in FIG. 9, which shows a system architecture diagram of the power management unit 16 shown in FIG. 7 mentioned above. The power management unit 16 is used to provide the received power input to back end circuits (including the digital controller 100, the conditioning end wireless transmission unit 13, the stimulation unit 14, and the detection unit 15 as shown in FIG. 7). The power management system 16 includes a rectification unit 160, a voltage regulation unit 164 and a boost unit 162. The power input may be an input of solar energy, RF (Radio Frequency) energy, infrasonic energy, AC electrical energy or piezoelectric vibration energy etc. It is noted particularly that the system architecture of the power management unit 16 according to the invention is not limited to the example shown in FIG. 9. In other words, in another example of the power management unit 16, the power management unit 16 is used for rectifying an input energy to a DC voltage lower than the input to perform a power supply process for the back end circuits, only the rectification unit 160 and the voltage regulation unit 164 are required. For example, a phone may be utilized to generate an energy through a headphone jack channel, and convert an audio AC signal into a DC voltage via the rectification unit 160. In a further example of the power management unit 16, as the power management unit 16 according to the invention is used for rectifying an input energy to a DC voltage higher than the input to perform the power supply process for the back end circuits, only the boost unit 162 and the voltage regulation unit 164 are required. Variations differ depending on required implementations.

Figure 10:
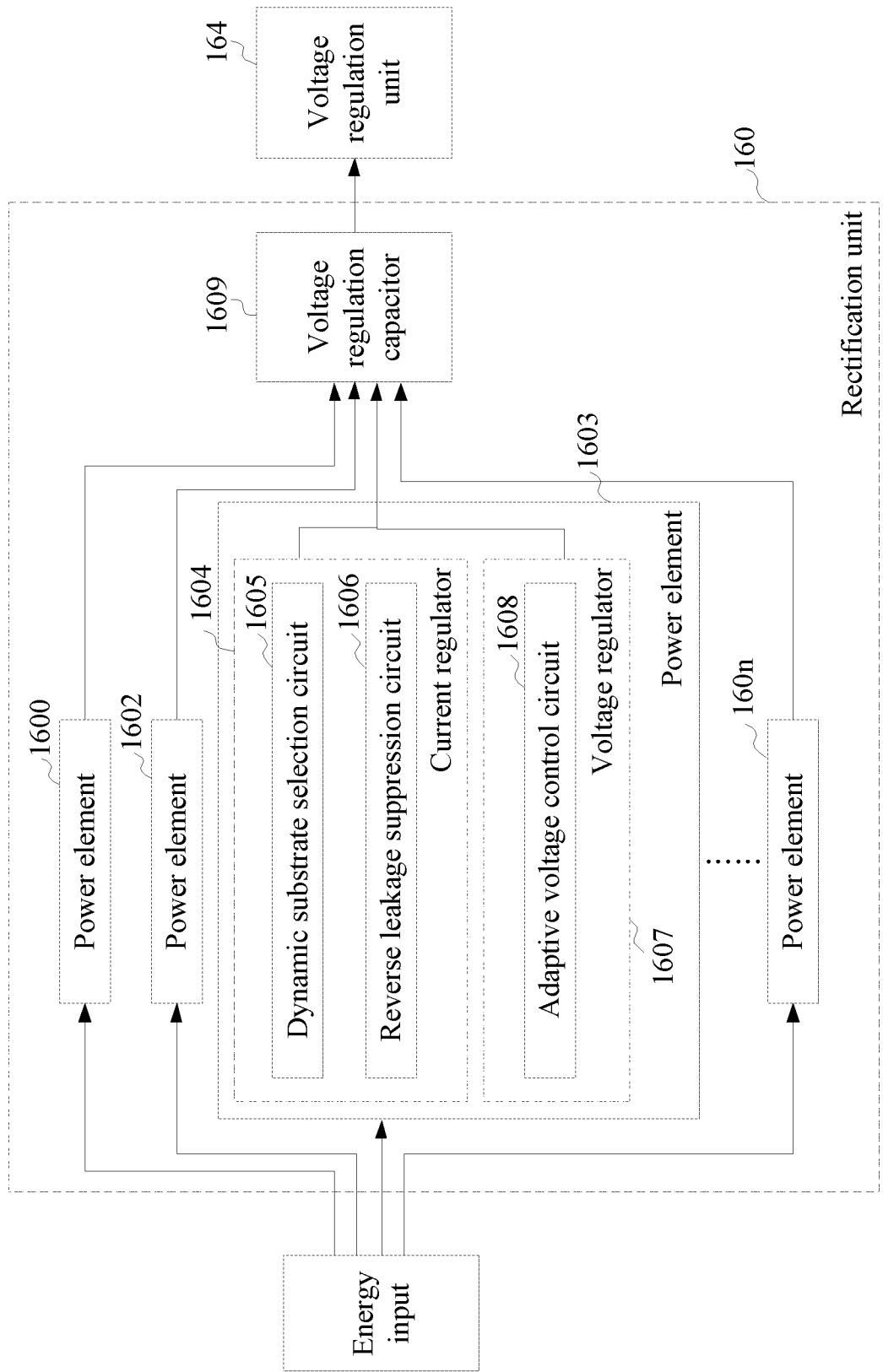
FIG. 10 is a system block diagram showing built-up members of a rectification unit shown in FIG. 9.

Refer to FIG. 10 in conjunction, which shows a basic architecture for the rectification unit 160 shown in FIG. 9. The rectification unit 160 in this example is, for example, a full-wave bridge rectifier. The rectification unit 160 includes numerous power elements (1600~160*n*) and a voltage regulation capacitor 1609 for reducing output voltage ripple. Each power element (1600~160*n*) of the rectification unit 160 includes a transistor capable of conduction path switching, a current regulator 1604 as well as a voltage regulator 1607, wherein the current regulator 1604 and the voltage regulator 1607 are used for addressing leakage current and latch up of substrate of MOS transistors of the conventional full-wave bridge rectifier. As shown in Figure, a current regulator 1604 includes a dynamic substrate selection circuit 1605 and a reverse leakage current suppression circuit 1606, while a voltage regulator 1607 has an adaptive voltage control circuit 1608, wherein an input energy is the multiplication of an input voltage and an input current, while an output energy is the multiplication of an output voltage and an output current. The power elements (1600~160*n*) are used to switch an input energy by utilizing a conduction path, and an DC voltage to be output is rectified to a low ripple DC voltage via the voltage regulation capacitor 1609. The current regulator 1604 selects a substrate potential dynamically through a dynamic substrate selection circuit to reduce leakage current due to parasitic transistor, and the reverse leakage current suppression circuit 1606 is utilized to switch the power element at a local end rapidly to reduce transient reverse leakage current and current consumption of the power element 1603 on the local end for input waveform, such that the output current is maximized. The voltage regulator 1607 utilizes a transistor to discharge an auxiliary capacitor through the adaptive voltage control (AVC) circuit 1608 for reducing the conduction resistance of the power element 1603 at the local end, reducing the voltage difference between the input voltage and the output voltage, and reducing the loss of the power element 1603 on the local end, such that the output voltage is maximized. Therefore, a high energy conversion efficiency rectifier is achieved.

Figure 11:
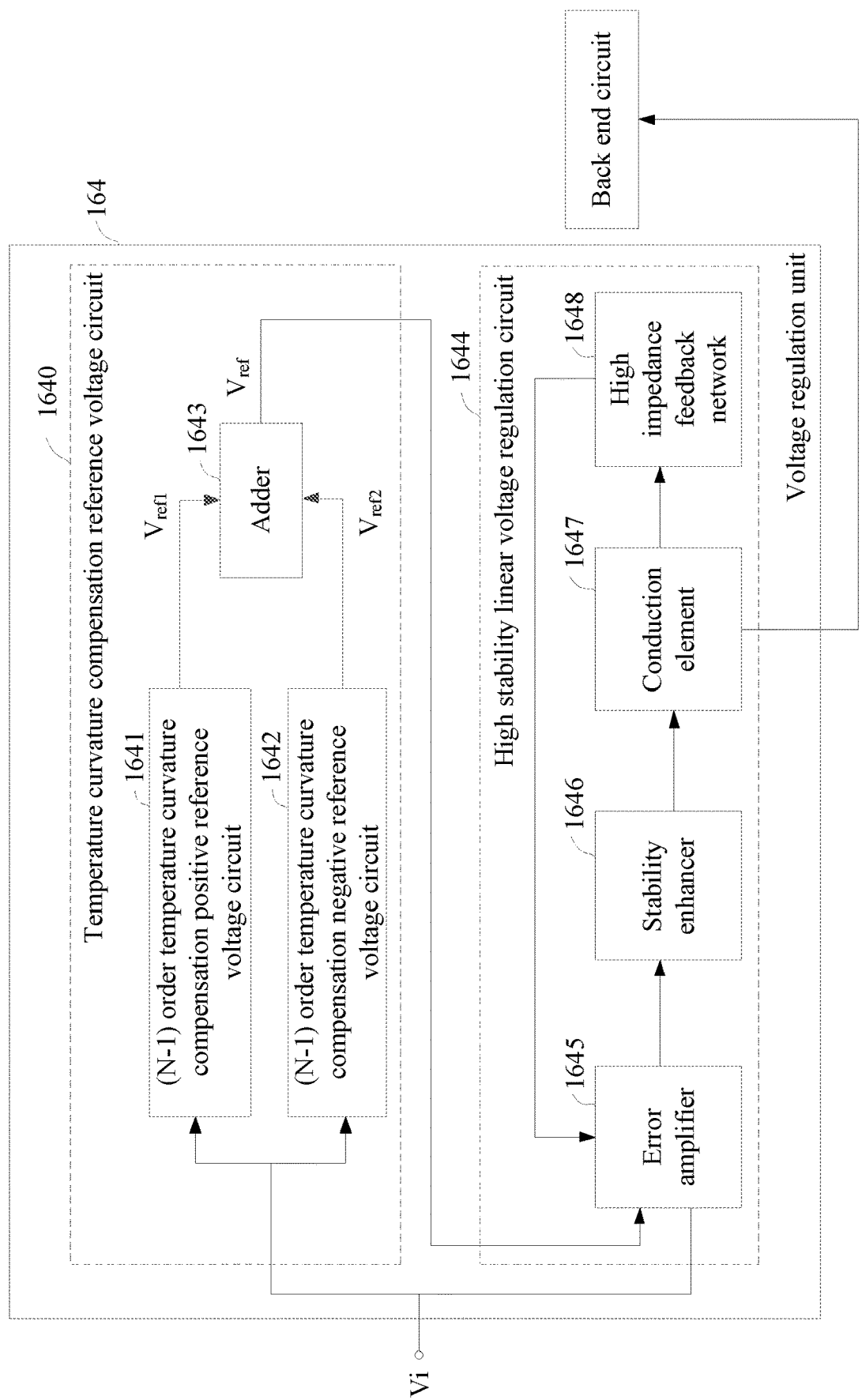
FIG. 11 is a system block diagram showing built-up members of a voltage regulation unit shown in FIG. 9.

Next, refer to FIG. 11 in which a block diagram of system for the voltage regulation unit 164 shown in FIG. 9 is shown. The voltage regulation unit 164 of this example is a low dropout linear regulator (LDO). The voltage regulation unit 164 includes a temperature curvature compensation reference voltage circuit 1640 and a high stability linear voltage regulation circuit 1644. The temperature curvature compensation reference voltage circuit 1640, which is characterized by low voltage, high power voltage rejection ratio, low power consumption and low temperature coefficient, is applicable to an environment with large variation of temperature range. The temperature curvature compensation reference voltage circuit 1640 includes a (N−1) order temperature curvature compensation positive reference voltage circuit 1641, a (N−1) order temperature curvature compensation negative reference voltage circuit 1642 and an adder 1643. The temperature curvature compensation reference circuit 1640 starts operation thereof with trigger of an input voltage Vi. The (N−1) order temperature curvature compensation positive reference voltage circuit 1641 is used to generate a (N−1) order temperature curvature compensation positive reference voltage which is positively correlated with temperature, and the (N−1) order temperature curvature compensation negative reference voltage circuit 1642 is used to generate a (N−1) order temperature curvature compensation negative reference voltage which is negatively correlated with temperature, while the adder 1643 uses the (N−1) order temperature curvature compensation positive reference voltage and the (N−1) order temperature curvature compensation negative reference voltage to perform a compensation mechanism for adding up currents, in order for achieving a N order temperature curvature compensation reference voltage Vref applicable to a large temperature range.

As shown in FIG. 11, the high stability linear voltage regulation circuit 1644, which is characterized by low voltage, high power voltage rejection ratio, low quiescent current, high stability, low area and low cost, and is applicable to an integrated chip, includes an error amplifier 1645, a stability enhancer 1646, a conduction element 1647 and a high impedance feedback network 1648. A DC voltage output from the voltage regulation capacitor 1609 of the rectification unit 160 will act as the power for the temperature curvature compensation reference voltage circuit 1640 and the high stability linear voltage regulation circuit 1644. The N order temperature curvature compensation reference voltage Vref processed by the temperature curvature compensation reference circuit 1640 and the feedback voltage output from the high impedance feedback network 1648 are delivered into the error amplifier 1645, and the conduction voltage output for conducting the conduction element 1647 is adjusted by the error amplifier 1645. The stability enhancer 1646 is inserted between the error amplifier 1645 and the conduction element 1647 to enhance the stability of the entire circuit. An input voltage with ripple is converted into a steady DC voltage for the back end circuits by the conduction element 1647. As the output voltage changes with unloading of the back end circuits, the output voltage is fed back to the error amplifier 1645 and the stability enhancer 1646 through the high impedance feedback network 1648 to adjust the output voltage, and transferred to the back end circuits via the conduction element 1647. Wherein, the error amplifier 1645 operates in a low bias current mode and the high impedance feedback network 1648 is implemented in a manner of a large impedance as a transistor in a cutoff region to achieve a low quiescent current.

Figure 12:
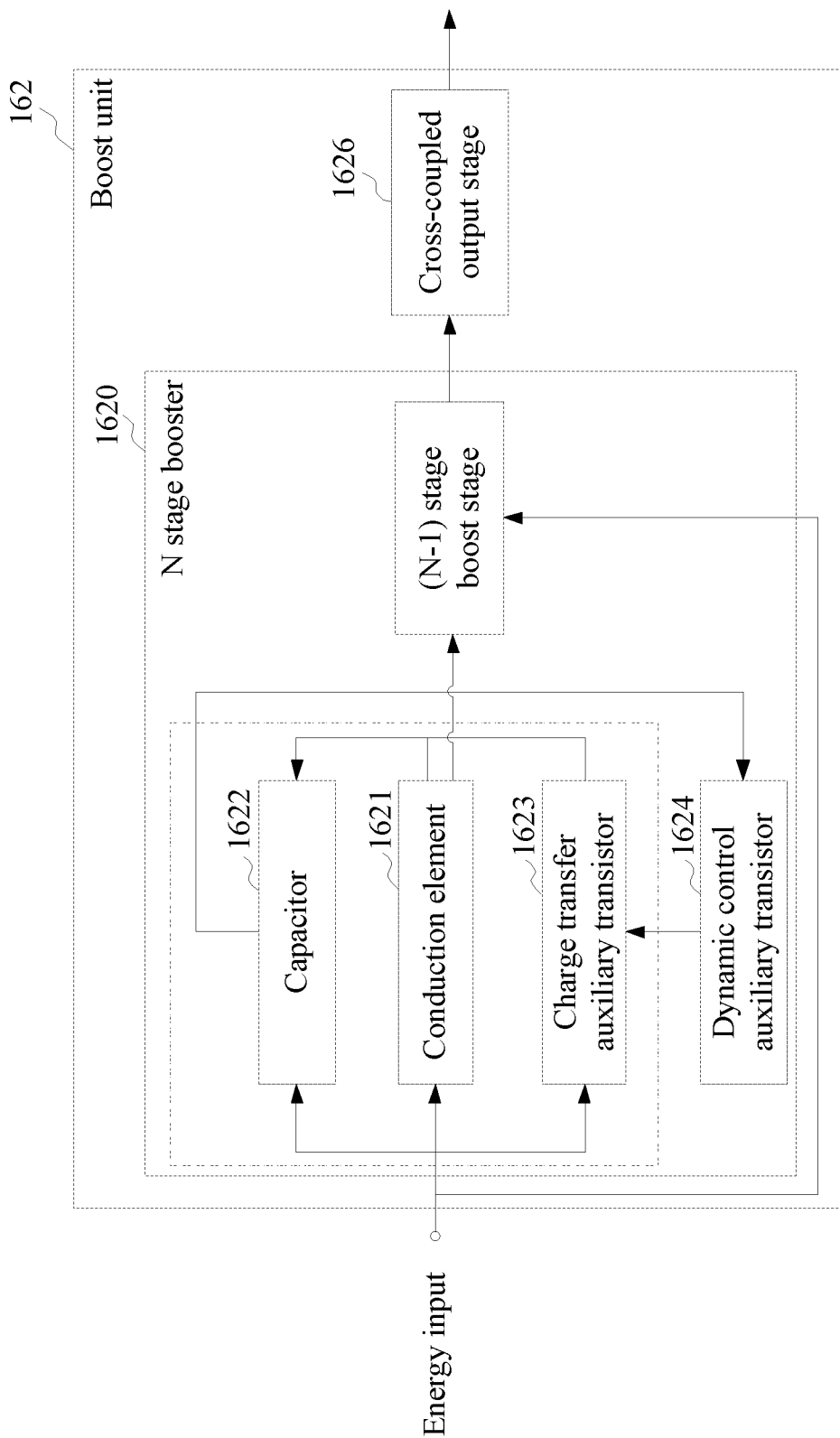
FIG. 12 is a system block diagram showing built-up members of a boost unit shown in FIG. 9.

Subsequently, refer to FIG. 9 again, the rectification unit 160 and the voltage regulation unit 164 mentioned above may apply the power management unit 16 to power supply processing of the conditioner 1' of low DC voltage. If the power management unit 16 is applied such that an input energy is rectified to a DC voltage higher than the input to perform power supply processing for the back end circuits mentioned above, such as a high-voltage stimulator of a biomedical system, the power processing may be performed by the boost unit 162 and the voltage regulation unit 164 of the power management unit 16. It should be noted that, in another example, if the power management unit 16 is used for rectifying the input energy to a DC voltage less than the input, in the path of the back end circuits for power supply process, the electrical signal process architectures for the voltage regulation units 164 in two paths for a DC voltage less than the input due to rectification and a high DC voltage are consistent. As shown in FIG. 11, for simplified illustration, the voltage regulation unit 164 is not described again here, but the boost unit 162 is further described below. As shown in FIG. 12, the boost unit 162, which is characterized by high voltage conversion efficiency, includes a N stage booster 1620, and a cross-coupled output stage 1626. A voltage is increased via the N stage booster 1620 for an input AC energy, and a required high voltage is output through the cross-coupled output stage 1626. The N stage booster 1620 includes a conduction element 1621, a capacitor 1622, a charge transfer auxiliary transistor 1623 and a dynamic control auxiliary transistor 1624 therein. The input energy is stored in the capacitor 1622 via the conduction element 1621. The output voltage is raised by changing a voltage on another end of the capacitor 1622. The across voltage of the conduction element 1621 is reduced with a high voltage at a back stage by utilizing the charge transfer auxiliary transistor 1623 in parallel with the conduction element 1621. The charge transfer auxiliary transistor 1623 will generate a reverse leakage current path under a transient condition, so that clocks are switched rapidly by utilizing the dynamic control auxiliary transistor 1624 for reducing the reverse leakage current of the charge transfer auxiliary transistor 1623 to increase energy conversion efficiency, while the cross-coupled output stage 1626 is intended to stabilize output and reduce ripple. Finally, a converted power signal with ripple removed is transferred to the voltage regulation unit 164 at a back end, in order for performing the temperature compensation as mentioned above, and converting and transmitting a steady DC voltage to the back end circuits.

In summary, the conditioner in the medical system capable of artificial intelligence and Internet of Things according to the present invention is provided for general people to use as a home medical device under operation with low power consumption, and is capable of Internet of Things to meet the requirement of remote medical treatment. Moreover, the disease analysis module of the control terminal device in the medical system provides multiple disease identification algorithms, which may assist a doctor in diagnosis. Further, the open loop unit and the closed loop unit of the digital controller in the conditioner provide an AI pre-processing to enable optimization of individualized stimulation effect.

The examples above are only illustrative to explain principles and effects of the invention, but not to limit the invention. It will be apparent to those skilled in the art that modifications and variations can be made without departing from the scope of the invention. Therefore, the protection range of the rights of the invention should be as defined by the appended claims.

What is claimed is:
1. A medical system capable of artificial intelligence and Internet of Things, including:
    a conditioner including:
        a stimulator used to perform stimulation processing on a physiological tissue to be stimulated;
        a detection unit for detecting a physiological signal of a physiological tissue to be detected;

a digital controller for performing digital signal processing on the physiological signal detected by the detection unit and analyzing a state of the stimulation processing performed on the physiological tissue to be stimulated to obtain a feedback result after the stimulation processing, the digital controller including:
a storage device storing conditioning parameter data for conditioning at least one physiological tissue, the control parameter data including: a first stimulation parameter value, a second stimulation parameter value and a predictable response signal;
an open loop circuit causing the stimulator to stimulate the physiological tissue to be stimulated according to the first stimulation parameter value stored in the storage device;
a closed loop circuit determining that: (a) when the stimulator performs the stimulation processing with the first stimulation parameter value and there is feeding back of the predictable response signal, the stimulator stimulates the physiological tissue to be stimulated with the first stimulation parameter value; the closed loop circuit determining that the stimulator performs the stimulation processing with the first stimulation parameter value but there is not feeding back of the predictable response signal, such that the stimulator stimulates the physiological tissue to be stimulated with the second stimulation parameter value when there is feeding back of the predictable response signal; (c) a feedback result with an abnormal message to be output if the closed loop circuit determines that the stimulator performs the stimulation processing with either the first or the second stimulation parameter value, the predictable response signal is not fed back; and
a conditioning end wireless transmission unit for wireless transmission of the feedback result processed by the digital controller, or wireless reception of the conditioning parameter data to be processed by the digital controller; and
a computation device including:
a cloud database for storing response values from stimulation performed on a plurality of physiological tissues with a plurality of stimulation parameter values;
a server module for accessing the cloud database, the server module providing a cloud user interface for inputting desired settings or storing an updated stimulation parameter value of the at least one physiological tissue, or updating the predictable response signal of the at least one physiological tissue, or for displaying the feedback result of at least one physiological tissue to be inquired and a stimulation parameter value used by the feedback result; and
a control terminal device including:
a near-end transmitter for performing data transmission processing with the conditioning end wireless transmission unit to perform an access action on the storage device;
a far-end transmitter for performing data transmission with the server module;
an intelligent processing module for processing data received by the near-end transmitter and the far-end transmitter, and controlling the near-end transmitter and the far-end transmitter to transmit data, as well as providing an end user interface, which displays the feedback result of the physiological tissue to be detected that is due to the physiological tissue to be stimulated being stimulated, received by the near-end transmitter, or sets up the updated stimulation parameter value with which the conditioner performs the stimulation processing, wherein the updated stimulation parameter value is transmitted to the digital controller through the near-end transmitter and the conditioning end wireless transmission unit for processing, wherein the digital controller that outputs the abnormal message uses a received updated stimulation parameter value for the stimulator to stimulate the physiological tissue to be stimulated, and the closed loop circuit determines whether there is feeding back of the predictable response signal when the stimulator stimulates the physiological tissue to be stimulated with the updated stimulation parameter value, such that the feedback result of the abnormal message is output if the predictable response signal is not fed back, which can let the intelligent processing module provide subsequent update processing on the conditioning parameter data according to the abnormal message.

2. The medical system according to claim 1, wherein the stimulator of the conditioner provides different stimulation approaches, including: an electrical stimulation, an optical stimulation and a magnetic stimulation, and a stimulation waveform of the stimulation approach can be a balanced bidirectional stimulation waveform, a balanced delay bidirectional stimulation waveform, an unbalanced bidirectional stimulation waveform, a unidirectional stimulation waveform or a balanced bidirectional stimulation waveform.

3. The medical system according to claim 1, wherein the conditioner is used to be arranged on a living body to be detected, and may be arranged within the living body or on an outer surface of the living body.

4. The medical system according to claim 1, wherein the physiological tissue to be detected has a same tissue body position as the physiological tissue to be stimulated.

5. The medical system according to claim 1, wherein the physiological tissue to be detected is a different tissue body position from the physiological tissue to be stimulated.

6. The medical system according to claim 1, wherein the control terminal device has a disease analysis module providing multiple disease identification algorithms for analyzing physiological signals and the feedback result transmitted by the conditioner to identify whether the feedback result transmitted by the conditioner is an abnormal signal and be capable of further identifying a disease type from the abnormal signal, which is provided in order to assist medical caring staff in diagnosis.

7. The medical system according to claim 1, wherein the conditioning end wireless transmission unit includes:
a wireless radio frequency transmission module including:
a pre-emphasis signal generator for shaping signal waveform of digital signals from the digital controller to obtain the feedback result after the stimulation processing to modulate the digital signals to form modulated output signals;
a current-reused self-mixing voltage-controlled oscillator for increasing voltage/current amplitude of the modulated output signals and reducing phase noise via a self-mixing technique; and
a current-reused multiple-transconductance power amplifier for amplifying the voltage/current amplitude of the modulated output signals via a current reuse technique, and transmitting the amplified modulated output signals through a first antenna to a wireless channel; and
a wireless radio frequency receiving module including:
a balun self-biasing gain-bandwidth-improved envelope detector for detecting carrier input signals received from a second antenna to obtain baseband signals and demodulating the baseband signals to form differential signals; and a current-reused cascode-two-stage amplifier for amplifying voltage/current amplitude of the differential signals in an open loop state to produce output signals, and transmitting the output signals to the digital controller.

8. The medical system according to claim 7, wherein the wireless radio frequency receiving module further includes a tunable high-pass filter for filtering off low frequency noise from the differential signals.

9. The medical system according to claim 7, wherein the wireless radio frequency receiving module further includes a comparator for detecting the output signals amplified by the current-reused cascode-two-stage amplifier, converting the output signals into digital data, and transmitting the digital data to the digital controller.

10. The medical system according to claim 1, wherein the detection unit includes: an analog front end signal processing module and a sigma-delta modulation analog-to-digital conversion module, wherein the analog front end signal processing module includes: a preamplifier, which receives and amplifies the physiological signal; an analog filter, which receives and filters an amplified sensing signal to generate a filtered signal; a postamplifier, which receives and amplifies the filtered signal to generate a dynamic range required to meet a subsequent sigma-delta modulation analog-to-digital conversion module, and the filtered signal is converted into a digital physiological signal by the sigma-delta modulation analog-to-digital conversion module for the digital controller to perform digitalization processing.

11. The medical system according to claim 10, wherein the sigma-delta modulation analog-to-digital conversion module compares the physiological signal to be output to the digital controller for processing with a physiological signal transmitted by the analog front end signal processing module and calculates multiple sets of dynamic range curves by a dynamic extension algorithm, based on which the digital controller extracts a suitable combination of system orders and feedforward coefficients for storage, the digital controller inputs a preset signal and gives a set of system orders and feedforward coefficients for system circuit adjustment and initialization, a strength of a signal output by the sigma-delta modulation analog-to-digital conversion module is monitored dynamically, when the digital controller monitors that a change in a strength of the output physiological signal does not exceed a preset value, initial feedforward coefficients and system orders are maintained, otherwise, the feedforward coefficients and system orders are switched until the system is stable and a power/performance balance is reached.

12. The medical system according to claim 1, wherein the conditioner further includes a power management unit, the power management unit including:

a rectification unit for rectifying an input energy to a DC voltage lower than an input in order to perform a power supply process for the digital controller, the conditioning end wireless transmission unit, the stimulator, and the detection unit, wherein the rectification unit includes:

a plurality of power elements for rectifying a voltage to a DC voltage by switching a conduction path for the input energy, each power element including a transistor capable of conduction path switching, a current regulator having a dynamic substrate selection circuit and a reverse leakage current suppression circuit as well as a voltage regulator having an adaptive voltage control circuit, wherein the dynamic substrate selection circuit selects a substrate potential of the transistor capable of conduction path switching dynamically to reduce a substrate leakage current of the transistor capable of conduction path switching, and the reverse leakage current suppression circuit is utilized for switching a power element at a local end to reduce transient reverse leakage current and current consumption of the power element at the local end for an input voltage, such that an output current for the power element at the local end is maximized; the adaptive voltage control circuit is used to increase a conduction voltage for lowering a conduction resistance, increasing switching speed when the power element at the local end is conducted in order to improve conversion performance;

a voltage regulation capacitor for outputting the DC voltage rectified by the power elements as a DC voltage with low ripple, and a first voltage regulation unit for stabilizing and transferring a DC voltage output by the rectification unit to the digital controller, the conditioning end wireless transmission unit, the stimulator, and the detection unit as a power supply.

13. The medical system according to claim 12, wherein the first voltage regulation unit includes: a first temperature curvature compensation reference voltage circuit and a first high stability linear voltage regulation circuit, the first temperature curvature compensation reference voltage circuit including: a first (N−1) order temperature curvature compensation positive reference voltage circuit, a first (N−1) order temperature curvature compensation negative reference voltage circuit and a first adder, the first temperature curvature compensation reference circuit performing temperature compensation according to a DC voltage output from the voltage regulation capacitor of the rectification unit, wherein the first (N−1) order temperature curvature compensation positive reference voltage circuit is used for generating a (N−1) order temperature curvature compensation positive reference voltage positively correlated with a temperature, the first (N−1) order temperature curvature compensation negative reference voltage circuit is used for generating a (N−1) order temperature curvature compensation negative reference voltage negatively correlated with a temperature, and the first adder is used for adding up the first (N−1) order temperature curvature compensation positive reference voltage and the first (N−1) order temperature curvature compensation negative reference voltage to output a first temperature curvature compensation reference voltage, in order to be applicable for a temperature range of N order temperature curvature compensation reference voltage.

14. The medical system according to claim 12, wherein the first voltage regulation unit further includes: a first high stability linear voltage regulation circuit, which includes: a first error amplifier, a first stability enhancer, a first conduction element and a first high impedance feedback network, the first error amplifier receives a DC voltage output from a voltage regulation capacitor of the rectification unit, a first temperature curvature compensation reference voltage output from the first temperature curvature compensation reference voltage circuit, and a feedback voltage output from the first high impedance feedback network, as well as adjusts a conduction voltage which is output for conducting the first conduction element, while the first stability enhancer is arranged between the first error amplifier and the first conduction element to enhance a stability of an entire circuit, and a steady DC voltage is converted from a received input voltage by the first conduction element for the digital controller, the conditioning end wireless transmission unit, the stimulator, and the detection unit, wherein as an output DC voltage changes with the digital controller, the conditioning end wireless transmission unit, the stimulator, and the detection unit, the output DC voltage is fed back to the first error amplifier and the first stability enhancer through the first high impedance feedback network for adjusting the output DC voltage, and transferred to the digital controller, the conditioning end wireless transmission unit, the stimulator, and the detection unit via the first conduction element.

* * * * *